Aug. 31, 1965 R. KORDES Plant Pat. 2,550
ROSE PLANT
Filed April 29, 1964
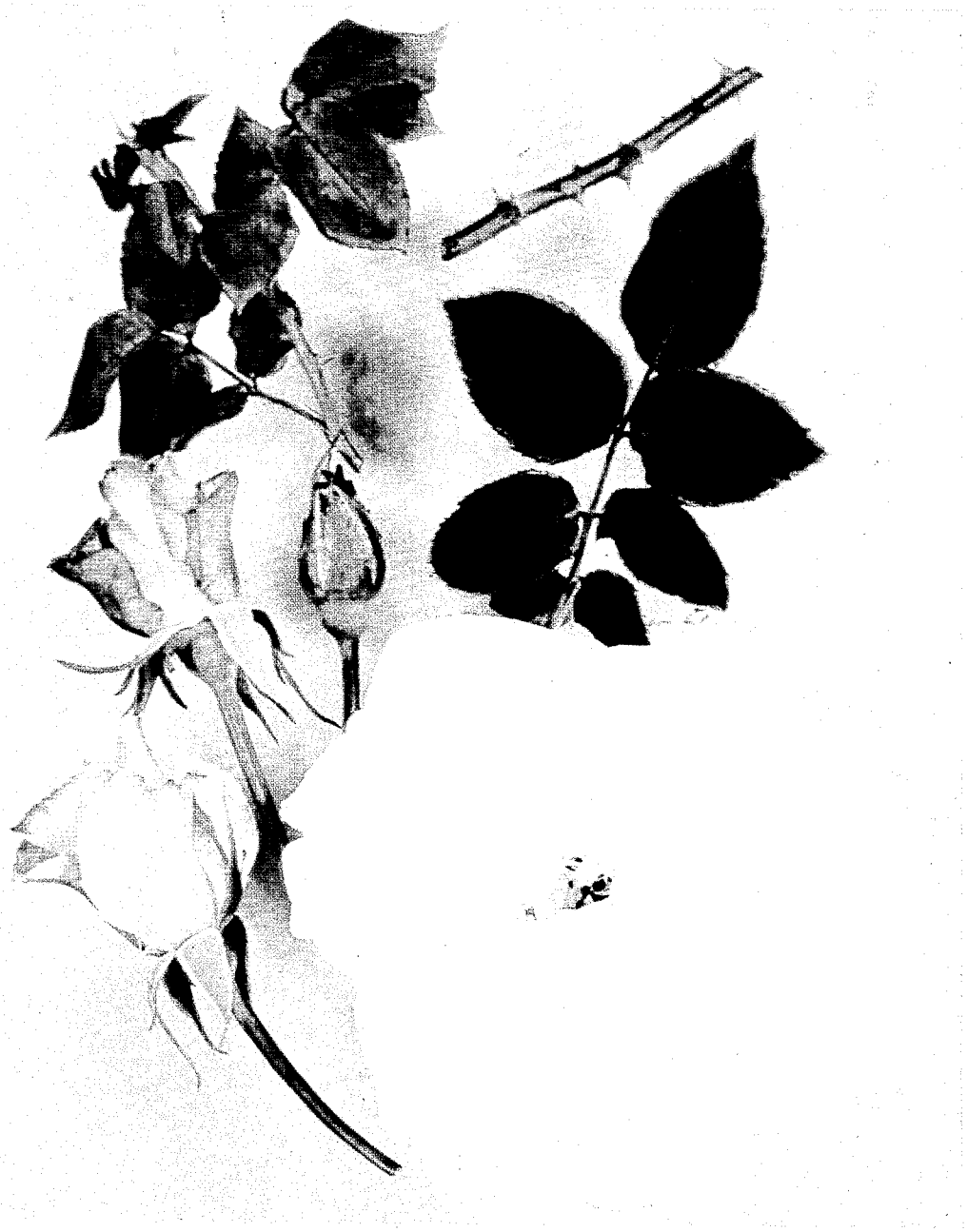
Inventor.
Reimer Kordes
By: Robb & Robb
Attorneys.

United States Patent Office

Plant Pat. 2,550
Patented Aug. 31, 1965

2,550
ROSE PLANT

Reimer Kordes, Barmstedt, near Elmshorn, Germany, assignor to Jackson & Perkins Company, Newark, N.Y., a corporation of New York Filed Apr. 29, 1964, Ser. No. 363,691
1 Claim. (Cl. Plt.—16)

The present invention relates to a new and distinct variety of rose plant of the hybrid tea class, which was originated by me by crossing the hybrid tea variety known as "Chantre" (unpatented) with the hybrid tea variety known as "Golden Sun" (unpatented).

The primary objective of this breeding was to produce a new rose variety in which there is combined a strong plant habit, with large flowers in a golden orange color. This objective was fully achieved, as evidenced by the following unique combination of characteristics which are outstanding in the new variety and distinguish it from its parents, as well as from all other varieties of which I am aware:

(1) A vigorous and strong habit of growth;
(2) Abundant production of large flowers; and
(3) A distinctive and attractive general color tonality of the buds corresponding to Nopal Red, very lightly overcast with Scarlet-Red, which finishes in the open flowers as Light Orange-Yellow, lightly overcast with Salmon-Orange.

Asexual reproduction of the new variety by budding, as performed at Newark, New York, U.S.A., and also at Pleasanton, California, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Chantre."
*Pollen parent.*—"Golden Sun."
Classification:
*Botanic.*—Hybrid tea.
*Commercial.*—Hybrid tea.

*Flower*

(Observations made from specimens grown outdoors at Newark, New York, U.S.A., in the early morning during the middle of the month of September.)

Blooming habit: Recurrent—continuous.
Bud:
*Size.*—Large.
*Form.*—Pointed; is not affected by wet or hot weather.
*Color.*—When sepals first divide—Nopal Red, Plate 1, with lower half of petal lightly overcast with Light Orange-Yellow, Plate 3. When petals begin to unfurl—Nopal Red, Plate 1, very lightly overcast with Brazil Red, Plate 1. When half-blown: inside of petals—Nopal Red, Plate 1, very lightly overcast with Scarlet Red, Plate 1; reverse of petals —Strawberry Pink, Plate 1, lightly overcast with Light Orange-Yellow, Plate 3, toward the base of the petal.
*Sepals.*—Slightly branched; curl back when petals begin to unfurl. Color: inside—Pale Turtle Green, Plate 32; outside—Biscay Green, Plate 17.

*Calyx.*—Color—Biscay Green, Plate 17. Shape—apple. Size—broad. Aspect—smooth. Odor when rubbed—none.
*Peduncle.*—Length medium. Aspect—smooth. Color—Yellowish Citrine, Plate 16. Strength—erect; heavy.
*Opening.*—Opens up well; is not affected by adverse weather conditions.

Bloom:
*Size.*—Large. Average size when fully expanded—from 5 inches to 5½ inches.
*Borne.*—Both singly and several together; high production of flowers.
*Stems.*—Long; strong.
*Form (when first open).*—High-centered. Permanence—retains its form to the end.
*Petalage.*—Double (full but open center). Number of petals under normal conditions—from 30 to 35.
*Color.*—Center of flower—Grenadine Red, Plate 2, very lightly overcast with Salmon-Orange, Plate 2. Outer petals—Pale Orange-Yellow, Plate 3, with lower half of petal lightly overcast with Light Orange-Yellow, Plate 3. Base of petal (aiglet)—Capucine Buff, Plate 3. Inside of petals—Light Orange-Yellow, Plate 3, lightly overcast with Salmon-Orange, Plate 2. Reverse of petals—Pale Orange-Yellow, Plate 3, very lightly overcast with Orange-Buff, Plate 3. General tonality from a distance—Light Orange-Yellow, Plate 3, lightly overcast with Salmon-Orange, Plate 2.
*Discoloration.*—General tonality at end of first day —Light Orange-Yellow, Plate 3, lightly overcast with Salmon-Orange, Plate 2. Second day—Light Orange-Yellow, Plate 3, lightly overcast with Salmon-Orange, Plate 2. Third day—Light Orange-Yellow, Plate 3, very lightly overcast with Salmon-Orange, Plate 2.

Petals:
*Texture.*—Leathery; is not affected by wet or hot weather.
*Appearance.*—Inside—satiny. Outside—shiny.
*Form.*—Oval; slightly notched.
*Arrangement.* — Imbracated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower —long.

*Genital organs*

Stamens, anthers: Medium size; many; regularly arranged around styles. Color — Light Ochraceous-Salmon, Plate 15.
Stamens, filaments (threads): Medium length. Color—Light Coral Red, Plate 13.
Pollen: Color—Naphthalene Yellow, Plate 16.
Styles: Bunched; uneven length; short; thin.
Stigmas: Color—Barium Yellow, Plate 16.
Ovaries: All enclosed in calyx.
Hips: None.
Seeds: None.

*Plant*

Form: Bush.
Growth: Vigorous and strong; upright.
Foliage: Compound of 5–7 leaflets.
*Size.*—Medium.
*Quantity.*—Normal.
*Color.*—New foliage: upper side—Light Bice Green, Plate 17, with edges of leaf and mid-rib Carmine, Plate 1; under side—Citrine, Plate 4, lightly overcast with Carmine, Plate 1. Old foliage: upper side—Varley's Green, Plate 18; under side—Light Cress Green, Plate 31.

*Shape.*—Oval pointed.

*Texture.*—Upper side—leathery. Under side—smooth.

*Ribs and veins.*—Ordinary.

*Edge.*—Serrated (saw toothed).

*Serration.*—Both double and single; small.

*Leaf stem.*—Color—Garnet Brown, Plate 1. Under side—smooth.

*Stipules.*—Medium length; smooth.

Wood:

*New wood.*—Color—Courge Green, Plate 17. Bark—smooth.

*Old wood.*—Color—Light Elm Green, Plate 17. Bark—smooth.

Thorns:

*Thorns.*—Quantity: on main stalks from base—ordinary; on laterals from stalk—ordinary. Form —narrow base; short; hooked downward. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous and strong habit of growth, abundant production of large flowers, and a distinctive and attractive general color tonality of the buds corresponding to Nopal Red, very lightly overcast with Scarlet-Red, which finishes in the open flowers as Light Orange-Yellow, lightly overcast with Salmon-Orange.

No references cited.

ABRAHAM G. STONE, *Primary Examiner.*